(12) United States Patent
Beyersdorff et al.

(10) Patent No.: US 7,118,580 B1
(45) Date of Patent: Oct. 10, 2006

(54) INSTRUMENT FOR INSERTING INTERVERTEBRAL IMPLANTS

(75) Inventors: Boris Beyersdorff, Tuttlingen (DE); Thierry Marnay, Montpellier (FR)

(73) Assignee: Spine Solutions Inc., West Chester, PA (US)

( * ) Notice: Subject to any disclaimer, the term of this patent is extended or adjusted under 35 U.S.C. 154(b) by 0 days.

(21) Appl. No.: 10/070,823

(22) PCT Filed: Sep. 14, 1999

(86) PCT No.: PCT/EP99/06803

§ 371 (c)(1),
(2), (4) Date: Jul. 15, 2002

(87) PCT Pub. No.: WO01/19295

PCT Pub. Date: Mar. 22, 2001

(51) Int. Cl.
*A61B 17/00* (2006.01)
*A61F 2/46* (2006.01)
*A61F 2/44* (2006.01)

(52) U.S. Cl. .................... 606/99; 623/17.15

(58) Field of Classification Search ............ 606/57, 606/61, 86, 90, 99, 100, 104, 105, 205, 206, 606/207, 208; 623/17.11, 17.14, 17.15, 17.16; D24/133, 135, 140; 81/358; 254/97
See application file for complete search history.

(56) References Cited

U.S. PATENT DOCUMENTS

| | | | |
|---|---|---|---|
| 114,816 A * | 5/1871 | Hiestand ................... 254/97 |
| 3,486,505 A | 12/1969 | Morrison |
| 3,875,595 A | 4/1975 | Froning |
| 4,467,802 A * | 8/1984 | Maslanka .................. 606/206 |
| 4,545,374 A | 10/1985 | Jacobson |
| 4,863,476 A | 9/1989 | Shepperd |
| 4,997,432 A | 3/1991 | Keller |
| 5,122,130 A | 6/1992 | Keller |
| 5,228,455 A * | 7/1993 | Barcel ...................... 607/127 |
| 5,314,477 A | 5/1994 | Marnay |
| 5,370,697 A | 12/1994 | Baumgartner |
| 5,383,888 A * | 1/1995 | Zvenyatsky et al. ....... 606/206 |
| 5,395,317 A | 3/1995 | Kambin |
| 5,401,269 A * | 3/1995 | Buttner-Janz et al. ... 623/17.15 |
| 5,409,492 A | 4/1995 | Jones et al. |
| 5,431,658 A | 7/1995 | Moskovich |
| 5,501,654 A * | 3/1996 | Failla et al. ............... 600/204 |
| 5,505,732 A | 4/1996 | Michelson |
| 5,507,816 A * | 4/1996 | Bullivant ................. 623/17.15 |
| 5,562,736 A | 10/1996 | Ray et al. |
| 5,571,109 A | 11/1996 | Bertagnoli |
| 5,676,701 A * | 10/1997 | Yuan et al. .............. 623/17.15 |

(Continued)

FOREIGN PATENT DOCUMENTS

FR 2 718 635 7/1996

(Continued)

*Primary Examiner*—Corrine McDermott
*Assistant Examiner*—David Comstock
(74) *Attorney, Agent, or Firm*—Stites & Harbison PLLC; Marvin Petry

(57) ABSTRACT

In an insertion instrument for a three-piece intervertebral implant that includes an upper part that can be placed against a vertebra, a lower part that can be placed against the adjacent vertebra, and a pivot element that can be inserted between these two parts, the instrument having two arms, disposed side by side and supported pivotably relative to one another on one end, which at their free ends each have one retention device for the upper part and lower part, respectively, of the intervertebral implant, it is proposed that a longitudinal guide for the pivot element is disposed in one of the arms.

81 Claims, 5 Drawing Sheets

U.S. PATENT DOCUMENTS

| | | | |
|---|---|---|---|
| 5,720,751 A * | 2/1998 | Jackson | 606/86 |
| 5,722,977 A | 3/1998 | Wilhelmy | |
| D401,335 S * | 11/1998 | Koros et al. | D24/133 |
| 5,885,300 A | 3/1999 | Tokuhashi et al. | |
| 5,888,226 A * | 3/1999 | Rogozinski | 623/17.16 |
| 6,063,088 A | 5/2000 | Winslow | |
| 6,083,225 A | 7/2000 | Winslow et al. | |
| 6,102,950 A | 8/2000 | Vaccaro | |
| 6,113,602 A | 9/2000 | Sand | |
| 6,117,174 A | 9/2000 | Nolan | |
| 6,126,660 A * | 10/2000 | Dietz | 606/61 |
| 6,126,674 A | 10/2000 | Janzen | |
| 6,146,421 A * | 11/2000 | Gordon et al. | 623/17.15 |
| 6,171,339 B1 | 1/2001 | Houfburg et al. | |
| 6,296,647 B1 * | 10/2001 | Robioneck et al. | 606/105 |
| 6,368,350 B1 * | 4/2002 | Erickson et al. | 623/17.14 |
| 6,436,139 B1 * | 8/2002 | Shapiro et al. | 623/17.11 |
| 6,712,819 B1 * | 3/2004 | Zucherman et al. | 606/61 |

FOREIGN PATENT DOCUMENTS

FR  2 737 656  2/1997

* cited by examiner

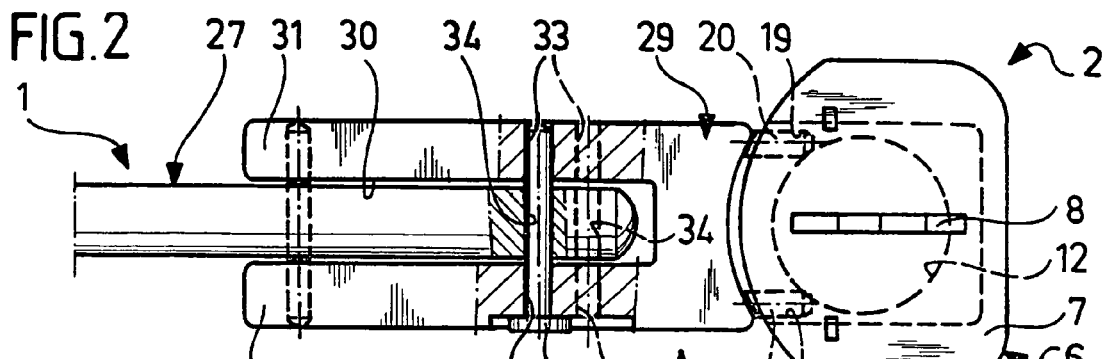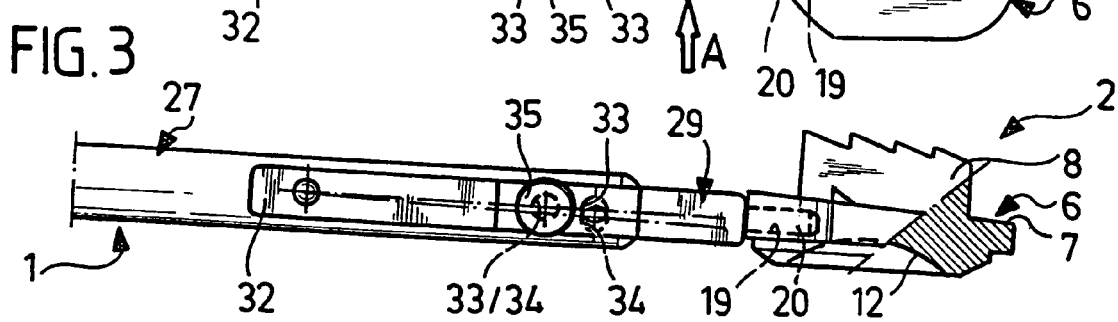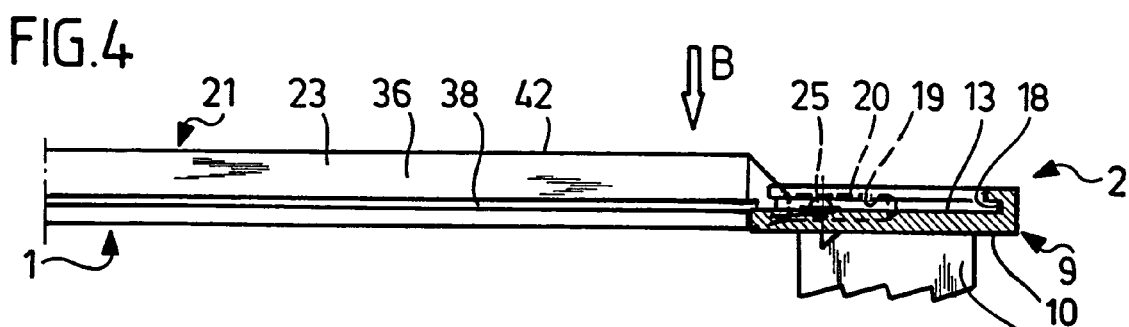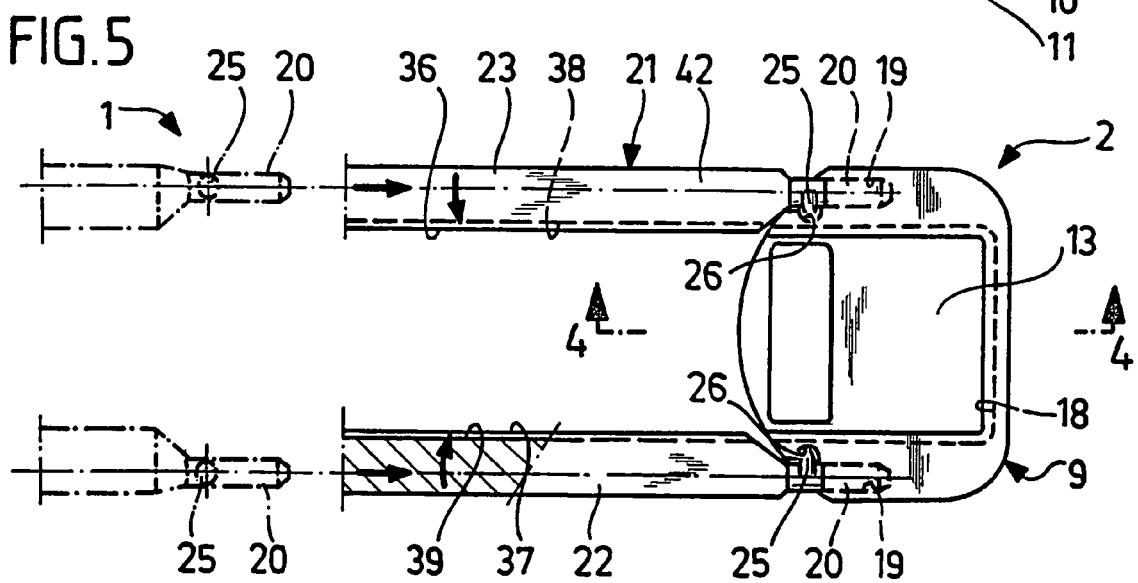

INSTRUMENT FOR INSERTING INTERVERTEBRAL IMPLANTS

The invention relates to an insertion instrument for a three-piece intervertebral implant that includes an upper part that can be placed against a vertebra, a lower part that can be placed against the adjacent vertebra, and a pivot element that can be inserted between these two parts, having two arms or levers, disposed side by side and supported pivotably at one end relative to one another, and each having at its other, free end one retention device for the upper part and lower part, respectively, of the intervertebral implant. The insertion instrument is also referred to as a medical device installation tool.

One such insertion instrument is known for instance from U.S. Pat. No. 5,314,477. The insertion instrument is embodied in the manner of tongs and can also be used, after the insertion of the upper and lower parts of the intervertebral implant, to move the two vertebrae apart to gain space for introducing the pivot element. In the known instrument, this pivot element must be introduced into the space between the upper and lower parts of the intervertebral implant by using other instruments. This is a difficult process in which there is the risk that the pivot element will be introduced tilted relative to the other two parts of the implant and will thus be damaged.

For inserting complete intervertebral implants, it is also known to move them along a longitudinal guide as far as the implant point and then to feed them out of the guide into the intervertebral space (U.S. Pat. No. 5,571,109). Such an instrument is suitable only for inserting complete intervertebral implants; moreover, the problem arises of an accurate adjustment of this guide relative to the intervertebral space: if there are maladjustments, the intervertebral implant could be inserted skewed, which can cause injuries.

It is the object of the invention to provide an insertion instrument, which may also be referred to as a medical device installation tool, of the type generically defined at the outset in such a way that these disadvantages are avoided and the introduction of the pivot element is simplified.

According to the invention, in an insertion instrument of the type described, this object is attained in that a longitudinal guide for the pivot element is disposed in one of the arms.

What is obtained thereby is a combined insertion instrument, which is used first to manipulate the upper and lower parts of the implant, and with which the upper and lower parts can be brought to the desired position inside the intervertebral space. As a result of the pivotable support of the arms, the upper part and lower part can then be moved apart from one another in a manner known per se, when the pivot axis acts as a fulcrum thus widening the intervertebral space, so that an introduction space for the pivot element is created between these parts. The pivot element is then inserted directly into this introduction space via the guide in one of the two arms, also known as levers, of the insertion instrument; by the connection of the two arms of the insertion instrument with the parts of the implant inserted into the intervertebral space, a reliable adjustment of the longitudinal guide for the pivot element is assured; moreover, it is assured that the pivot element will be introduced into the intervertebral space exactly in the desired relative position to the other two parts of the implant.

Both the insertion of the upper part and lower part of the implant and the introduction of the pivot element can thus be done with a single instrument; it is no longer necessary to disengage an instrument and replace it with another instrument; this insertion instrument performs a greater number of functions, namely that of inserting the upper part and lower part of the intervertebral implant, that of widening the intervertebral space, and finally that of introducing the pivot element into the space between the upper part and lower part of the implant.

It is favorable if the longitudinal guide is formed by protrusions engaging longitudinal grooves.

For instance, it can be provided that grooves opposite one another, which are engaged by lateral protrusions of the pivot element, are disposed in one of the arms, in a receiving chamber for the pivot element, the receiving chamber extending in the longitudinal direction of the arm.

In an especially preferred embodiment, it is provided that the arm or lever having the longitudinal guide has two rodlike legs, disposed parallel to and spaced apart from one another, and which between them form a receiving chamber for the pivot element and which guide the pivot element between them longitudinally of the receiving chamber.

It is favorable if the longitudinal guide, on its end adjacent to the pivotally supported end of the arms, forms an insertion region, where the pivot element can be inserted into the longitudinal guide. This insertion region can for instance be formed in such a way that longitudinal grooves are open at the face end; in another exemplary embodiment, it can be provided that the longitudinal guide does not begin until at a distance from the pivotally supported end that corresponds to the length of the pivot element to be inserted.

In an especially preferred embodiment, the longitudinal guide of the one arm changes over into a longitudinal guide of the part of the intervertebral implant that is retained on that arm. A continuous longitudinal guide for the pivot element is thus obtained on the one hand along the arm and on the other hand also along the first part of the intervertebral implant, so that an absolutely precise introduction of the pivot element into the attached part of the intervertebral implant is assured. During the insertion process, this part of the implant connected to the arm practically forms a part of the insertion instrument; after the introduction of the pivot element, this part is detached from the insertion instrument and remains in the intervertebral space as part of the implant.

In a further preferred embodiment, the insertion instrument includes a push member or pusher block, which is insertable into the longitudinal guide and is joined to a rodlike thrust element or pusher rod. Using this member, the pivot element can be advanced as far as the intervertebral space along the longitudinal guide.

It is especially advantageous if, according to a preferred embodiment of the invention, the two arms are disposed side by side at their free ends, in such a way that the retention devices overlap one another in the direction of the pivoting motion of the arms. As a result, a very low structural height of the insertion instrument, which is on the order of magnitude of the gap width of the intervertebral space, can be achieved, and it is furthermore possible as a result for the two parts of the implant, which are joined by the arms of the insertion instrument, to be guided quite close together and as a result to achieve a very low structural height. In this way, these two parts of the implant can be introduced into the intervertebral space without major widening of the intervertebral space; the widening of the intervertebral space takes place only after these parts of the intervertebral implant have been introduced, by the pivoting apart of the arms that hold these two parts of the implant.

It is advantageous if the pivotally supported ends of the two arms, i.e., the proximal handle portion of the arms or levers, have a spacing from one another such that the arms, in their insertion position of the upper part and the lower part of the intervertebral implant, in which the free ends of the arms, i.e., the distal portion of the arms or levers, are at their closest proximity to one another, have a greater spacing from one another on the supported end than on the free end. Once again, this contributes to making the structural height of the insertion instrument, and the implant parts retained in it during insertion, as slight as possible.

Also in this arrangement according to a preferred embodiment, it is possible to provide a spreader element, which is braced on both arms and can be fed or advanced along the arms in the direction toward the free end of the arms, and in the process pivotally spreads the arms apart. Thus solely by advancing the spreader element along the arms, the widening of the intervertebral space is made possible, once the upper and lower parts of the intervertebral implant have been inserted into the intervertebral space.

It is favorable if at least one of the two arms has a longitudinal guide for the spreader element, so that this element is guided in a defined way along the arms.

Furthermore, a feed rod, also referred to as a pusher rod, can be disposed on the spreader element, with the aid of which the spreader element is displaced along the arms.

In an especially preferred embodiment, the feed rod is embodied as a rack, which meshes with a driving gear wheel in the region of the pivotally supported ends of the arms; this provides a very sensitive feeding motion of the spreader element along the arms, and even major forces can be transmitted via the toothed connection.

The retention devices, with which the implant parts are retained in the arms, can be embodied in quite different ways; a design in which the retention devices are pins that engage openings of the upper part and lower part of the intervertebral implant, respectively, is especially preferred.

In a preferred embodiment, the retention devices on at least one of the arms are pivotable about a pivot axis that is located in the region of the free end of the arm and extends parallel to the pivot axis of the arm, and the retention devices, after being pivoted about this pivot axis, can be locked in different angular positions. As a result, it is possible to vary the inclination of the two implant parts relative to one another slightly, for instance in the range from 1 degree to 5 degrees, so that along with the implant height, the implant angle can also be selected to suit the correct positioning of the vertebrae.

In a preferred embodiment, for locking the angular position, a fixation pin can be provided, which can be inserted into bores oriented at different angular positions to one another.

In a further preferred embodiment, at least one retention device has a releasable locking means. As a result of this releasable locking means, the implant part retained on the arm is connected undetachably to the arm; only after this locking means is unlocked is it possible to separate the implant part from its insertion instrument.

As a result, unintentional separation of the insertion instrument from the implant parts is averted; it is even possible in this way for already-implanted implant parts to be pulled back out of the intervertebral space, should that be necessary.

It is favorable if the locking is effected by rotating a locking bar about an axis of rotation, which axis extends substantially parallel to the longitudinal axis of the arm on which the retention device is disposed.

In particular, in a preferred embodiment, the arm carrying the retention device, or a part of this arm, is rotatable about its longitudinal axis and carries a locking bar, which in one position non-releasably locks the part of the intervertebral implant retained on the retention device to the arm on which the retention device is disposed and in another position releases it.

An especially advantageous embodiment is obtained if the retention device is a pin engaging a receiving bore on the retained part of the intervertebral implant, and the locking bar is a protrusion protruding laterally from this pin, which in one angular position of the pin engages a corresponding recess of the implant part, but in another angular position emerges from this recess.

In an especially preferred embodiment, the arm having the longitudinal guide has two parallel legs, wherein the space between them forms a receiving chamber for the pivot element, and the other arm extends centrally between these legs, so that its free end can move between the legs.

It can furthermore be provided that a spreader element, disposed between the arms and displaceable along them, rests on the surface of the two legs and, with its protrusion, it reaches between the two legs to engage the receiving chamber. As a result, guidance of the spreader element along the arms is obtained.

In addition, the spreader element, on its top, can have an indentation into which the arm moves. Once again, this contributes to the guidance of the spreader element.

The legs of the one arm can be rectangular in cross section; the other arm can be circular in cross section.

The ensuing description of preferred embodiments of the invention serves the purpose of more detailed explanation in conjunction with the drawing.

FIG. 2 is a top plan view of the upper arm of the insertion instrument of FIG. 1 with the upper part of the intervertebral implant retained on it;

FIG. 3 is a side view in the direction of the arrow A in FIG. 2;

FIG. 4 is a side view, taken along line 4—4 of FIG. 5, of the lower arm with the lower part of the intervertebral implant retained on it;

FIG. 5 is a top plan view of the lower arm, taken in the direction of the arrow B in FIG. 4;

Figure 1:
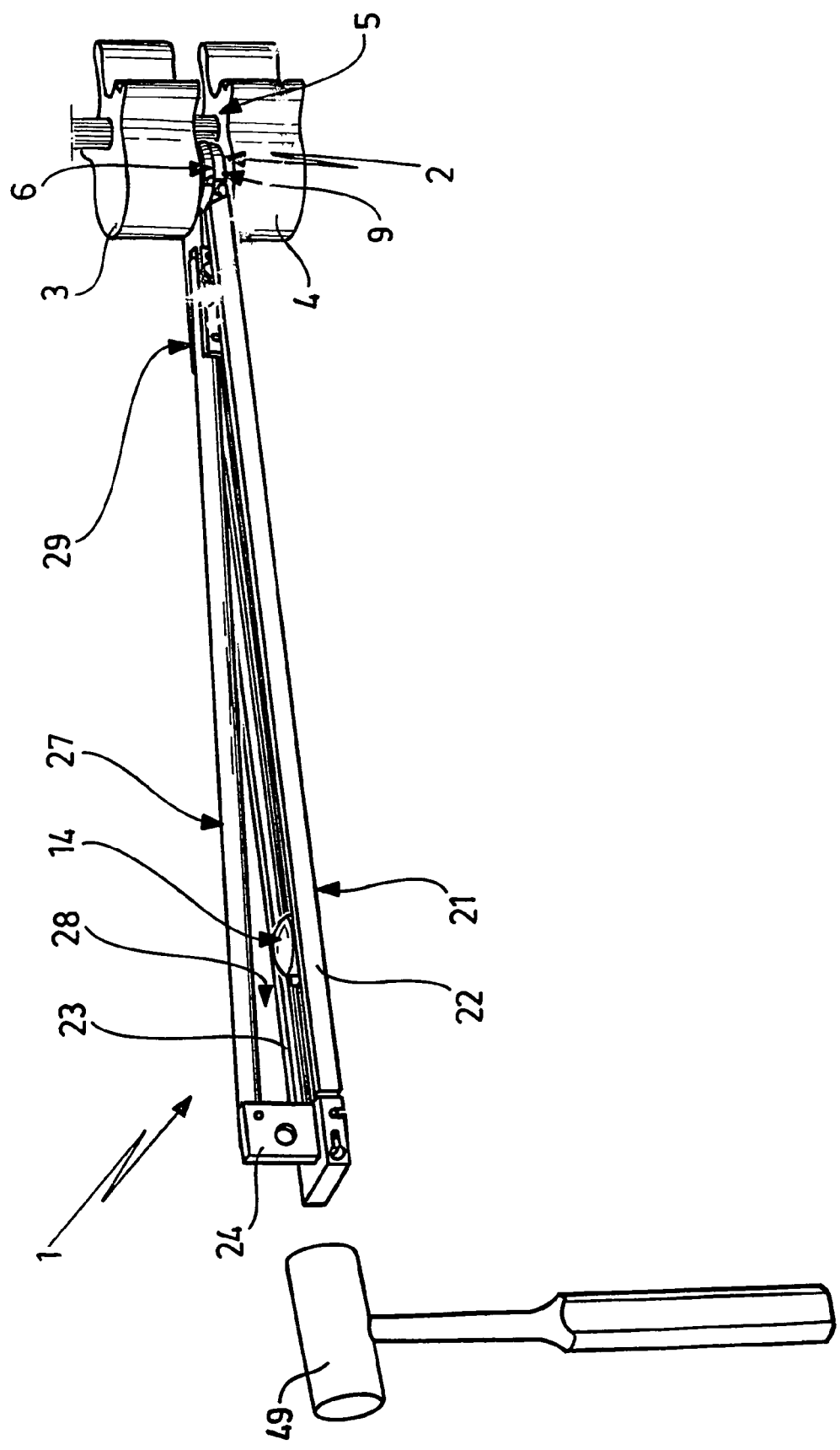
FIG. 1 is a perspective view of the insertion instrument after the introduction of the upper part and lower part of an intervertebral implant into the intervertebral space, before the spreading of the intervertebral space and before the introduction of the pivot element into the intervertebral space.

The insertion instrument 1 shown in the drawing is used to insert an intervertebral implant 2 into the intervertebral space 5 defined by two vertebrae 3, 4.

The intervertebral implant 2 includes a substantially plate-shaped upper part 6 with an upper flat contact face 7 and anchoring elements 8 protruding from it, and an also plate-shaped lower part 9 with a flat outer contact face 10 and anchoring elements 11 protruding from that face.

The upper part 6, on its side toward the lower part 9, has a dome-shaped bearing face 12; an indentation 13 is machined into the lower part 9 and is open toward one side and forms an insertion space for a pivot element 14 that also forms part of the intervertebral implant 2. This pivot element 14 has a plate-shaped, substantially rectangular base 15 and a bearing protrusion 16, protruding centrally from it on one side, whose upper side forms a dome-shaped bearing face 17.

The pivot element 14 can be inserted into the indentation 13 from the open side; the lateral edges of the base 15 engage lateral grooves 18 in the lower part 9, so that the pivot element 14 can be inserted, guided along these grooves 18, into the indentation 13.

In the implanted state, the bearing face 17 engages the concave bearing face 12 of the upper part, so that the upper part 6 and lower part 9 are braced on one another via the pivot element and are pivotable relative to one another.

Both the upper part 6 and lower part 9, on one side face, have insertion bores 19, extending parallel to the respective contact faces 7 and 10, and retaining pins 20 of the insertion instrument 1 can be inserted into these bores.

This insertion instrument 1 has a first elongated arm or first lever 21 with two spaced-apart parallel legs 22, 23, which are each retained at one end rotatably about its longitudinal axis on a bearing block 24 which provides a fulcrum on the proximate handle portion of the first arm 21. Both legs 22 and 23 have a square cross section and form rodlike long elements, which on the free end, along the extension of the axis of rotation of the legs each carry one of the retaining pins 20.

On these retaining pins 20 of the legs 22 and 23, radially protruding locking bar protrusions 25 are also provided, which can be embodied for instance as pins inserted radially into the retaining pins 20; these inserted pins in one angular position of the legs 22 engage lateral recesses 26 of the lower part 9, and these recesses 26 are open toward the upper part 6, so that by rotating the legs 22 and 23 by 90 degrees, the locking bar protrusions 25 can be rotated in such a way that they emerge from the recesses 26. As long as the locking bar protrusions 25 are engaging the recesses 26, the legs 22 and 23, when the retaining pins 20 have been inserted into the insertion bores 19, are releasably connected to the lower part 9, but if the locking bar protrusions 25 are rotated out of the recesses 26 by rotation of the legs 22 and 23, then the retaining pins 20 can be pulled out of the insertion bores 19, so that a displacement of the legs 22 and 23 relative to the lower part 9, and thus an insertion or separation become possible.

The legs 22 and 23 can be releasably fixed in their final positions by a detent engagement, not shown in the drawing, in which positions the locking bar protrusion 25 engages the recess 26 and emerges completely from the recess 26, respectively.

On the bearing block 24, spaced apart from the plane defined by the two legs 22 and 23, a second arm or lever 27 is pivotably supported about an axis of rotation that extends transversely to the longitudinal direction of the legs 22 and 23 and parallel to the plane defined by them; the arm 27 is disposed approximately midway between the two legs 22 and 23, so that the free end of the arm 27 can enter the space 28 between the two legs 22 and 23. Because of the spacing of the bearing location of the arm 27 from the plane defined by the legs 22 and 23, the spacing of the arm 27 from the arm 21 decreases continuously, as becomes clear from the illustration in FIG. 1, forming a fulcrum for turning of arm or lever 27 towards and away from the arm or levers 21. Together arms 21, 27 form two opposing levers of insertion instrument 1.

The arm 27 is circular in cross section and on its free end or distal portion it carries a U-shaped holder 29, which receives the free end of the arm 27 in the space 30 between two parallel legs 31, 32. In the region of the free end of the legs 31, 32, the holder 29 and the arm 27 are joined together in such a way that they can be pivoted about an axis of rotation extending parallel to the pivot axis of the arm 27. As result, the holder 29 can assume different angular positions relative to the arm 27; in FIG. 3, two angular positions differing by a small angular amount are shown in dot-dashed lines. For fixing the holder 29 in different angular positions, transverse bores 33 and 34, respectively, are provided both in the legs 31 and 32 and in the arm 27, and specifically a plurality of such pairs of transverse bores are offset in the longitudinal direction and are oriented with one another at various positions of the holder 29 relative to the arm 27. A fixation pin 35 can be inserted into these pairs of transverse bores 33, 34. Since in the various pairs the transverse bores 33, 34 that belong together can assume a different position, for each pair of transverse bores when a fixation pin 35 is inserted, a different angular position relative to the arm 27 results; the pivot angles are on the order of magnitude of a few degrees, and for instance a total range that can be between 1 degree and 5 degrees is covered.

Retaining pins 20 are disposed on the holder 29 and can be inserted as described into insertion bores 19 of the upper part 6. Because of the different angular position of the holder 29, it is possible to tilt the upper part 6 slightly relative to the lower part 9 that is retained on the legs 22 and 23.

Figure 6:
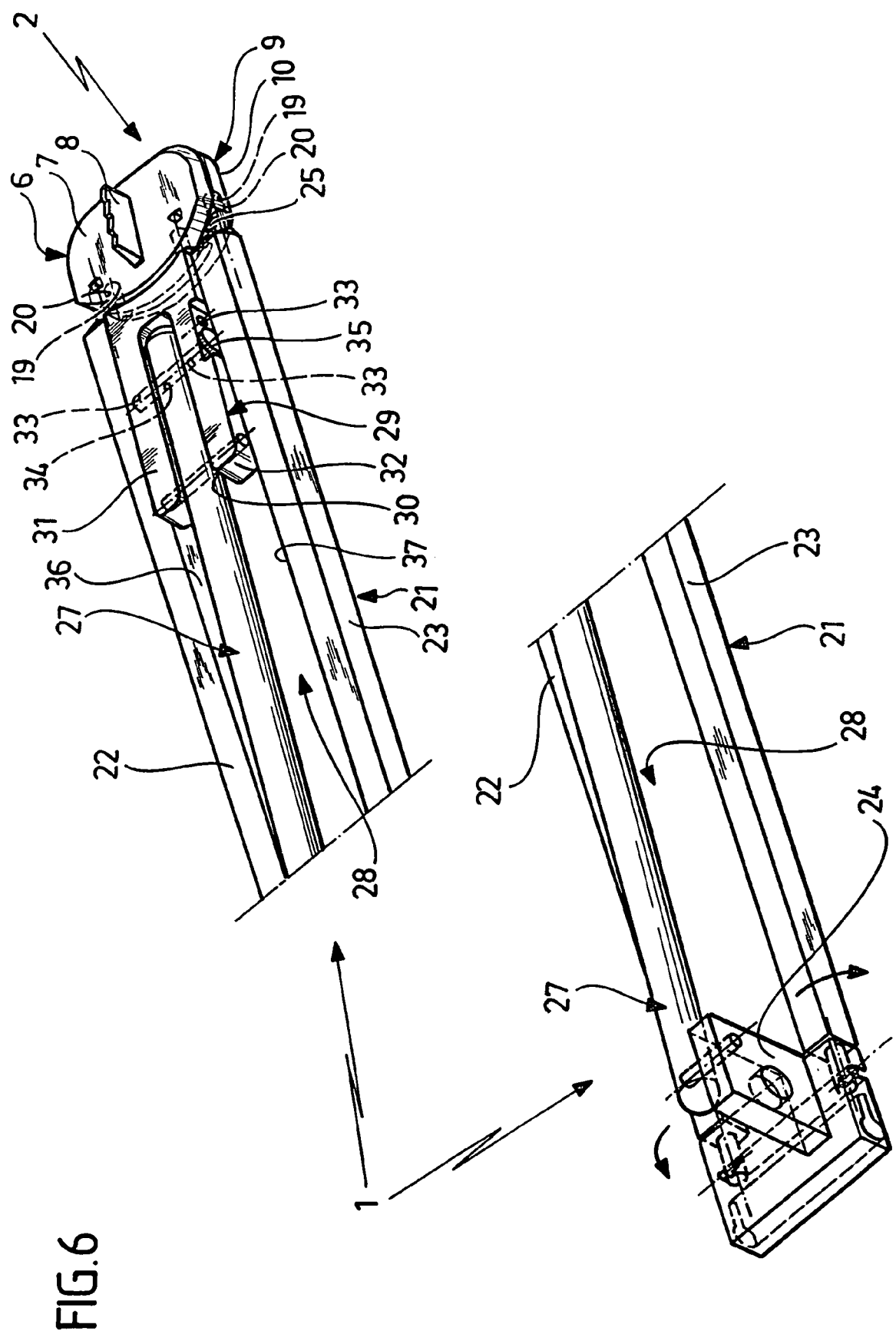
FIG. 6 is a perspective view of the insertion instrument with the upper part and lower part retained on it in the insertion position, with the implant parts at their closest proximity to one another.

The width of the holder 29 is selected such that the holder 29 fits into the space 28 between the two legs 22 and 23, so that the retaining pins 20 on the holder 29 and on the legs 22 and 23 can be disposed practically side by side; as a result, it is possible to retain the upper part 6 and lower part 9 in a position of closest proximity on the two arms 21 and 27; this position is designated as the insertion position (FIGS. 1 and 6).

When the locking bar protrusions 25 engage the recesses 26, the two legs 22 and 23, in the inside faces 36, 37 facing one another, have longitudinal grooves 38, 39, facing one another, which form a longitudinal guide for the pivot element 14. The dimensioning of these longitudinal grooves 38, 39 corresponds to that of the side edges of the base 15 of the pivot element 14, so that the pivot element 14 is guided longitudinally in the space 28 between the legs 22 and 23, when the side edges of the base 15 move into the longitudinal grooves 38 and 39. These longitudinal grooves 38 and 39 end at a distance in front of the bearing block 24 to enable an insertion of the base 15 into the longitudinal grooves 38, 39, and these longitudinal grooves 38 and 39 continue as far as the free end of the legs 22 and 23, where they merge directly with the grooves 18, disposed on both sides of the indentation 13, that serve to receive the base 15. What is thus obtained is a guide path for the pivot element 14 that leads from the legs 22 and 23 directly into the inside of the lower part 9 of the intervertebral implant 2.

A plate-like push member 40 (also referred to as a pusher block) is also insertable into the longitudinal grooves 38 and 39 and is pivotably connected to a pusher rod such as thrust rod 41. By means of this thrust rod 41, the pivot element 14, inserted into the longitudinal grooves 38 and 39, can be advanced along its guide path; to that end, the push member 40 is introduced after the pivot element 14 into the guide path formed by the longitudinal grooves 38 and 39.

A spreader element 43 that spans the space 28 between the two legs 22 and 23 is braced on the flat top side 42 of the legs 22 and 23; with a protrusion 44, it moves slightly into the space 28 and as a result is guided transversely to the longitudinal direction of the legs 22 and 23. This spreader element 43, on its end remote from the legs 22 and 23, has an indentation 45 of arclike cross section, into which the arm 27 moves. The spreader element 23 is connected to a thrust rod 46, embodied as a rack, which meshes with a gear wheel 47 that is supported rotatably on the bearing block 24 and can be rotated by means of a handle part 48 located at a proximal, handle portion of the opposed levers. Upon such rotation, the thrust rod 46 is displaced, which leads to a longitudinal displacement of the spreader element 43 along the legs 22 and 23. Upon such advancement of the spreader element 43, the arm 27 is as a result pivoted away from the legs 22 and 23; that is, the arms 27 and 21 (first and second levers) are spread apart via pivoting of their respective proximal handle portions about the fulcrum formed by bearing block 24, so that as a result the upper part 6 and lower part 9 are moved away from one another. This in turn leads to forcing the vertebrae 3 and 4 apart and thus to widening of the intervertebral space 5.

The insertion instrument described preferably comprises a biocompatible metal, such as titanium or a titanium alloy; the same is true for the upper part 6 and lower part 9 of the intervertebral implant 2. The pivot element 14 is made from a biocompatible plastic material, such as polyethylene, and the spreader element 43 is likewise preferably of a plastic material, so as to assure good sliding relative to the legs 22 and 23 and to the arm 27.

For insertion of the intervertebral implant 2 into an intervertebral space 5, first, after the disk has been removed from the intervertebral space 5, the intervertebral space is prepared in a suitable way; for instance, perpendicular grooves can be hammered into the vertebrae 3, 4 that receive the respective anchoring elements 8 and 11 of the intervertebral implant 2.

After suitable preparation, the upper part 6 and the lower part 9 are slipped onto the arms 27 and 21, respectively; the lower part 9 is locked to the arm 21 by rotation of the legs 22, 23, causing the locking bar protrusions 25 to engage the recesses 26 of the lower part 9 and the two arms 21 and 27 are pivoted into the insertion position, in which the upper part 6 and the lower part 9 are brought into their closest proximity; accordingly these two parts have a slight structural height. In this insertion position, the upper part 6 and lower part 9 are introduced into the prepared intervertebral space 5, for instance by being hammered in using a hammerlike instrument 49 (FIG. 1). The inclination that the upper part 6 assumes relative to the lower part 9 can be preselected by pivoting the holder 29 relative to the arm 27; in the desired position, the angular position is fixed by the fixation pin 35.

After this insertion of the upper part 6 and lower part 9, the pivot element 14 and the push member 40 are inserted successively into the guide path formed by the longitudinal grooves 38, 39; furthermore, both the push member 40 and the thrust rod 41 and the gear wheel 47 are inserted into the instrument.

Figure 7:
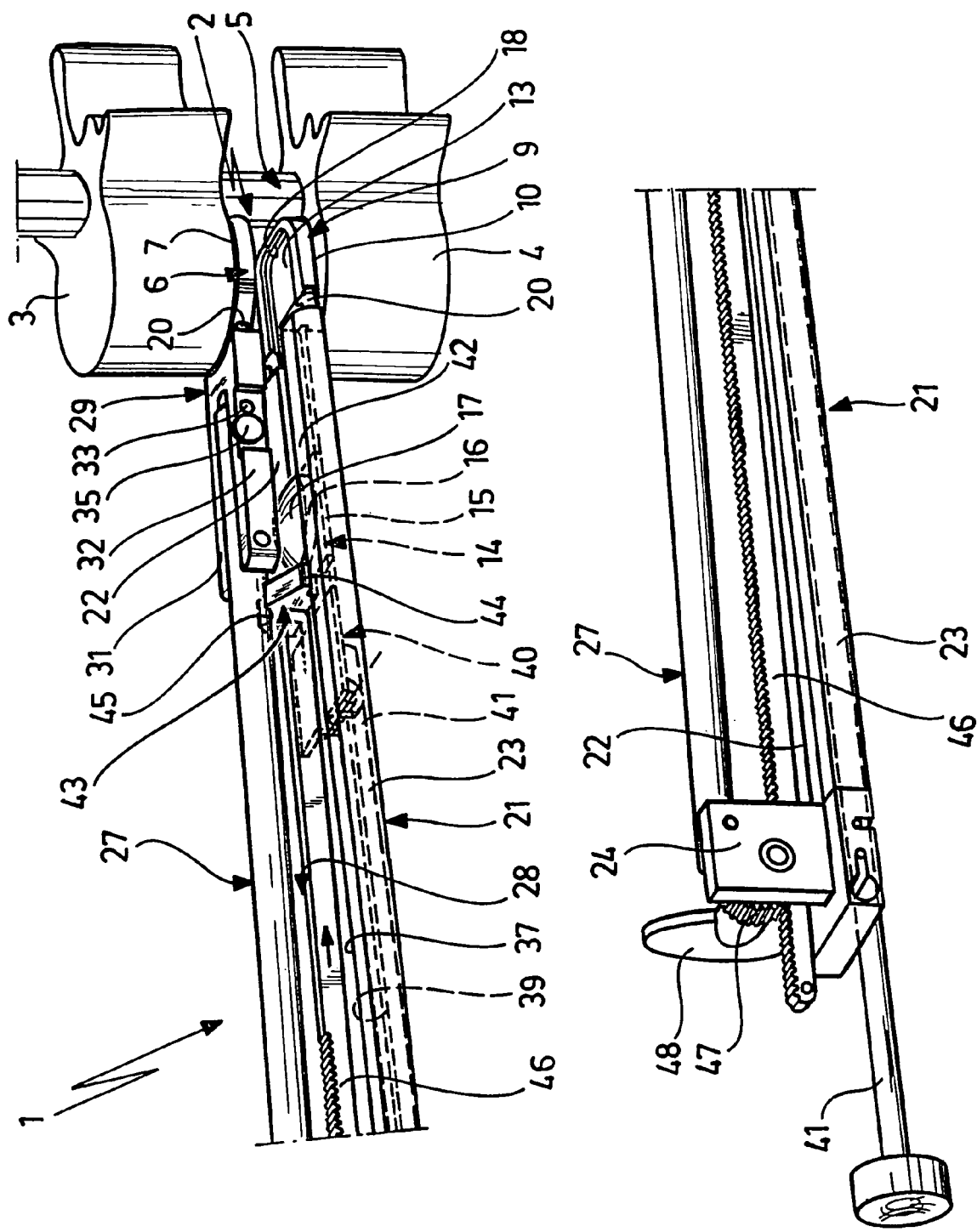
FIG. 7 is a perspective view of the insertion instrument of FIG. 6 after the insertion of the upper part and lower part of the intervertebral implant into the intervertebral space and after the widening of the intervertebral space, shortly before the pivot element is inserted between the upper part and lower part of the intervertebral implant.
Figure 8:
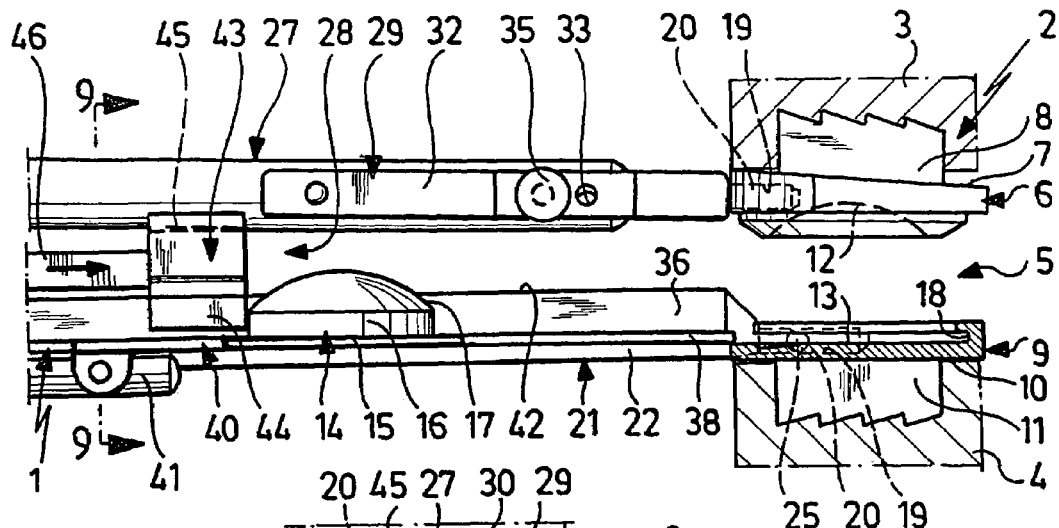
FIG. 8 is a side view of the insertion instrument of FIG. 7, shortly before the insertion of the pivot element between the upper part and lower part of the intervertebral implant.
Figure 9:
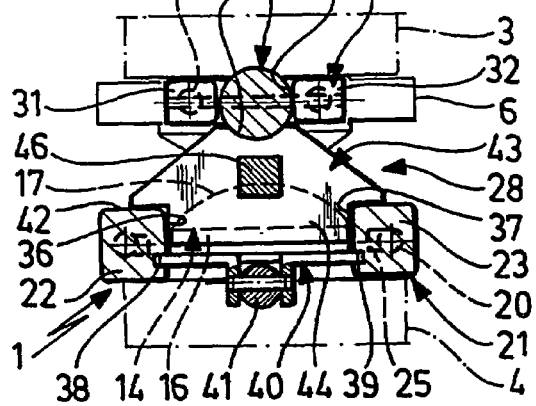
FIG. 9 is a sectional view taken along the line 9—9 of FIG. 8.
Figure 10:
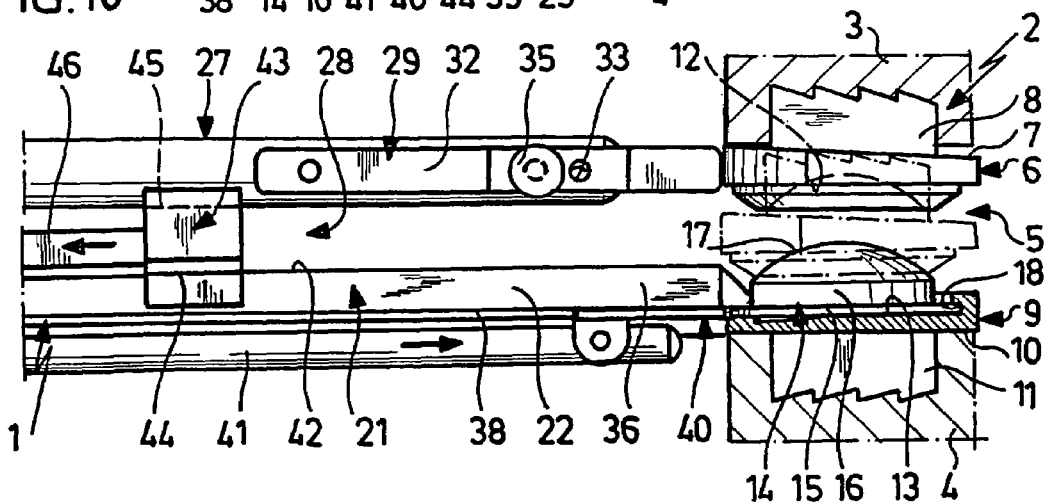
FIG. 10 is a view similar to FIG. 8 after the insertion of the pivot element between the upper part and lower part of the intervertebral implant.

By rotation of the gear wheel 47 and advancement of the spreader element 43, the arms 21 and 27 are spread apart; this leads to an increase in the mutual spacing between the upper part 6 and lower part 9, and thus to a widening of the intervertebral space 5 (FIGS. 7–9). The widening is selected to be great enough that by means of the push member 40, the pivot element 14 can be inserted into the indentation 13 in the lower part 9 (FIG. 10). Following that, by retraction of the spreader element 43, the spacing between the upper part 6 and lower part 9 is reduced again, until the bearing faces 12 and 17 engage one another and the parts of the intervertebral implant 2 have thus attained their final position (FIG. 10, dot-dashed outline of upper part 6).

By rotation of the legs 22 and 23 about their longitudinal axes, the engagement of the locking bar protrusions 25 and the recesses 26 is undone, and then the insertion instrument 1 can be pulled off the now properly inserted intervertebral implant 2.

The invention claimed is:

1. An implant insertion instrument in combination with a three piece intervertebral implant of the type that includes an upper part which can be placed against a vertebra, a lower part that can be placed against an adjacent vertebrae and a pivot element that can be inserted between the upper and lower parts, the instrument having two arms disposed adjacent each other and supported pivotally relative to one another at one end, each arm including at its free end opposite said one end a retention device for the upper part and the lower part, respectively, and including a longitudinal guide structure for the pivot element guided by at least one of said arms to push the pivot element.

2. The invention according to claim 1, wherein the longitudinal guide structure includes grooves and the pivot element includes lateral edges which engage said grooves.

3. The invention according to claim 2, wherein the grooves of the longitudinal guide structure face each other for receiving the pivot element for movement in the longitudinal direction of that arm.

4. The invention according to claim 1, wherein the arm having the longitudinal guide structure comprises two legs disposed parallel to and spaced apart from one another, the space between the legs forming a receiving chamber in which the pivot element is guided longitudinally along said arm.

5. The invention according to claim 1, wherein the longitudinal guide structure includes, near its end adjacent to the pivotal support of the arms, an insertion region whereat the pivot element can be inserted onto the longitudinal guide structure.

6. The invention according to claim 1, wherein the longitudinal guide structure includes grooves and wherein the lower part includes grooves which are aligned with the grooves on the longitudinal guide structure when that lower part is mounted on the free end of that arm, and wherein the grooves on the longitudinal guide structure and the grooves on the lower part are aligned with each other such that lateral edges of a pivot element can move directly from the grooves on the longitudinal guide structure into the grooves on the lower part.

7. The invention according to claim 1, including a pusher which is mounted on and slidable along the longitudinal guide structure for pushing the pivot element, and including an elongated rod extending from said pusher towards the pivotally supported ends of the arms.

8. The invention according to claim 1, wherein the two arms are disposed adjacent each other at their free ends and constructed such that the retention device on one of the arms is positioned adjacent to the retention device on the other arm.

9. The invention according to claim 1, wherein the two arms, at their pivotally supported ends, are spaced from one another such that the arms, in the insertion position in which the free ends of the arms are in their closest proximity to one another have a greater spacing from one another at their pivotally supported ends than at their free ends.

10. The invention according to claim 9, including a spreader element which is mounted on the arms for movement along the arms in the direction toward the free ends of the arms to move the two arms about their pivotal support away from each other.

11. The invention according to claim 10, wherein at least one of the two arms has a structure for receiving the spreader element, and including an elongated feed rod connected to the spreader element.

12. The invention according to claim 11, wherein the feed rod includes a rack which meshes with a driving gear wheel in the region of the pivotal support of the arms.

13. The invention according to claim 1, wherein the retention devices are pins which engage bores in the upper and lower parts, respectively.

14. The invention according to claim 1, wherein the retention device on at least one of the arms is rotatable about an axis that is located in the region of the free end of that arm and which extends parallel to the pivot axis at the pivotal support of that arm, and wherein the retention device, after being pivoted about this axis, can be locked in different angular positions.

15. The invention according to claim 14, including a fixation pin insertable into bores in that arm for locking the retention device at different angular positions.

16. The invention according to claim 1, wherein at least one of the retention devices has a releasable locking means for releasably locking its implant part thereon.

17. The invention according to claim 16, wherein locking of the releasable locking means is effected by rotating a locking bar about an axis of rotation, which axis extends substantially parallel to the longitudinal axis of the arm on which the retention device is mounted.

18. The invention according to claim 17, wherein at least a portion of the arm carrying the retention device is rotatable about its longitudinal axis to rotate the locking bar, such that in one position the locking bar of the arm locks the connected implant part and in another angular position of the arm, releases the connected implant.

19. The invention according to claim 18, wherein the retention device has a pin which engages a receiving bore on the connected implant part and the locking bar protrudes laterally from this pin to engage or disengage a notch on the connected implant part to lock or release it, respectively.

20. The invention according to claim 1, wherein the arm having the longitudinal guide structure comprises two parallel legs which form between them a receiving chamber for receiving the pivot element and wherein the other arm extends centrally between them so that its free end can dip between the parallel legs.

21. The invention according to claim 20, including a spreader element disposed between the two arms and displaceable along them, said spreader element resting on the surface of the two legs and having a protrusion which extends down between the two legs into the receiving chamber and an indentation on its top for receiving the other arm.

22. The invention according to claim 1, wherein a first of said arms comprises a pair of parallel legs and the second arm comprises a single rod located centrally between the two legs of the first arm, the two arms spaced apart at one end where they are pivotally supported, such that the other ends, which are said free ends, are movable about said pivotal support, towards and away from each other.

23. The invention according to claim 22, wherein said longitudinal guide structure comprises grooves on the sides of the legs of the first arm which face each other, and the pivot element has lateral edges which engage said grooves.

24. The invention according to claim 23, wherein the lower part which is mounted on the free end of said first arm has grooves that are aligned with the grooves on the legs, whereby the lateral edges of the pivot element are movable along the grooves of the legs and then into the grooves of the lower part.

25. The invention according to claim 24, including a pusher, also mounted in the grooves of the legs, a rod connected to the pusher, the pusher being movable along the grooves to push the pivot element therealong and into the lower part.

26. The invention according to claim 24, including a spreader element engaging the two legs of the first arm and the single rod of the second arm and positioned and shaped such that when moved along the arms toward the free ends, it spreads the arms apart from each other.

27. The invention according to claim 22, wherein, in the closest proximity of the upper and lower parts to each other, when mounted on the free ends of the arms, the second arm moves between the two legs of the first arm.

28. An implant insertion in combination with a three piece intervertebral implant, the instrument comprising:
a first arm which can engage a lower part of the implant and insert it into the intervertebral space,
a second arm operatively connected to the first arm and operable in coordination with the first arm to engage an upper part of the implant to insert it into the intervertebral space essentially concurrently with insertion of the lower part, and
guide structures operatively connected to and guided by the first and second arms for spreading apart the inserted upper and lower parts and inserting a third part between them.

29. The invention according to claim 28, said guide structures including a pusher for pushing the third part along the first arm, and a spreader for spreading the arms apart.

30. The invention according to claim 29, wherein the first arm comprises a pair of legs with longitudinal grooves facing each other, both third part and the pusher being mounted in said grooves to move along the arms, and wherein the spreader is mounted on said arms to spread the arms apart as it moves therealong.

31. The invention according to claim 30, wherein the lower part includes grooves aligned with the grooves of the legs, whereby the pusher can push the third part along the legs of the first arm and directly into the lower part.

32. The invention according to claim 30, wherein the upper and lower parts nest, one within the other, in their closest proximity, and the second arm comprises a single rod located centrally between the legs of the first arm, and said single rod of the second arm moves in between the legs of the first arm to accommodate the nested position of the upper and lower parts.

33. An insertion instrument in combination with a three piece intervertebral implant of the type having upper and lower parts which engage adjacent vertebrae and a third part located between the upper and lower parts,
the instrument having an arm structure which includes a pair of parallel legs which engage the lower part at an end thereof, opposed grooves facing each other along the parallel legs and opposed grooves facing each other on the lower part and which are aligned with the grooves in the parallel legs, the third part having lateral edges which engage the grooves of both the parallel legs and the lower part, the third part being movable along the grooves in the parallel legs and directly into the grooves in the lower part.

34. The invention according to claim 33, wherein the arm structure includes a first arm which comprises the parallel legs and a second arm which at its free end engages the upper part, the first and second arms being pivotally supported and spaced apart from each other at their ends remote from their implant engaging free ends.

35. The invention according to claim 34, including a spreading element movable along the first and second arms for spreading the first and second arms apart to provide a spacing between the upper and lower parts for insertion of the third part therebetween.

36. The invention according to claim 33, wherein the lower part has a recess formed by two side walls, an end wall and an open side opposite to the end wall, its grooves being formed in the side walls, whereby the third part enters the lower part through the open side.

37. An insertion instrument in combination with a three piece intervertebral implant of the type having upper and lower parts engaging adjacent vertebrae and a third part located between the upper and lower parts, a working space defined by parallel planes which pass through opposed outer surfaces of the upper and lower parts and are parallel to the direction of movement of the instruments when inserting said parts, upper and lower arms engaging respectively at their free ends, the upper and lower parts, an elongated spreader element for spreading the upper and lower parts apart, while in the intervertebral space, to allow insertion of the third part, an elongated pusher element for moving the third part along the arms and into place in the intervertebral space between the spaced apart upper and lower parts, and both of said arms, said spreader element and said pusher element being located and operable completely within said working space.

38. The invention according to claim 37, said lower arm comprising a pair of parallel legs, the space between said parallel legs being less than the distance between the said parallel planes, and the upper arm comprising a single rod located centrally between the two legs of the lower arm.

39. The invention according to claim 38, the pusher element comprising an elongated rod located and operable between the parallel legs for pushing the third part along the parallel legs and into the lower part.

40. The invention according to claim 39, the spreader element being located in a plane between the parallel legs and movable along the parallel legs of the lower arm and engaged on its top by the single rod of the upper arm.

41. The invention according to claim 38, the third part being a pivot element located between the parallel legs and movable along facing grooves located in the parallel legs under the action of the pusher element.

42. An insertion instrument in combination with a three piece intervertebral implant having upper and lower parts and a third part located between the upper and lower parts, which implant is insertable into an intervertebral space between adjacent vertebrae, the instrument comprising:

a working space defined by parallel planes which pass through opposed outer surfaces of the implant and are parallel to the direction of insertion movement of the implant into the intervertebral space, an elongated structure comprising a plurality of elongated arms for holding and inserting the implant, and wherein said elongated structure is located and operable completely within said working space.

43. The invention according to claim 42, wherein the implant includes a first part which engages one vertebrae of the intervertebral space and a second part which engages the other vertebrae of the intervertebral space, the two parts being moveable relative to each other within the intervertebral space.

44. The invention according to claim 43, wherein the plurality of arms include separate arms for engaging each of the two parts, all of which arms are located and operable completely within the working space.

45. The invention according to claim 11, wherein the implant includes a third part located, in use, between the first and second parts.

46. The invention according to claim 44, including a pusher for engaging the third part, said pusher also being moveable and operable completely within said working space.

47. The invention according to claim 44, wherein the separate arms for the upper and lower parts are mounted for pivotable movement relative to each other about an end remote from the ends which engage the first and second parts.

48. The invention according to claim 44, the implant including a third part located between the first and second parts, and wherein the pusher is moveable along at least one of said arms for engaging the third part, all arms and the pusher being located and operable completely within said working space.

49. An insertion instrument in combination with a three piece intervertebral implant of the type having upper and lower parts which engage adjacent vertebrae and a third part located between the upper and lower parts, said instrument including an upper arm for holding the upper part at its free end and a lower arm for holding the lower part at its free end, the upper and lower parts having complementary facing structures which allows them to come to a nested position in which their combined height is less than the total height of the upper and lower parts, taken separately, and the upper arm being movable vertically in relation to the lower arm such that they overlap, taken vertically, to allow said nesting of the upper and lower parts.

50. The invention according to claim 49, the lower arm comprising a pair of parallel legs, the upper arm comprising a single rod located and movable centrally between the legs of the lower arm, and wherein when the upper and lower arms overlap, the upper arm is located between the legs of the lower arm.

51. The invention according to claim 50, including a spreader for spreading the upper and lower arms apart to move the upper and lower parts from their nested position towards a spaced apart position, and including a longitudinal guide structure for receiving a third part and moving it along the parallel legs and into the space between the separated upper and lower parts.

52. An instrument for inserting an intervertebral implant of the type having upper and lower parts which engage adjacent vertebrae, an upper arm for holding the upper part and a lower arm for holding the lower part, the lower arm comprising a pair of elongated legs which engage the lower part at the free end thereof, and wherein at least one of the legs is rotatable relative to the lower part about its axis to move its free end between a locked position whereat it locks the lower part thereon and an unlocked position whereat the lower part is free to be removed from said free end.

53. An instrument according to claim 52, wherein both legs have pins at the ends thereof which each engage a bore in the lower part, the pin on said at least one rotatable leg having a protrusion extending perpendicular to the pin, and wherein in one rotational position of the rotatable leg, the protrusion engages an opening in the lower part to retain the lower part thereon, and in the other rotatable position of the leg, the protrusion releases the lower part.

54. An instrument according to claim 53, wherein both of said legs of the lower arm are rotatable and have pins, each with a protrusion at its free end and a corresponding opening in the lower part, and wherein the upper arm includes pins at its free end for engaging the upper part.

55. An insertion instrument in combination with a three piece intervertebral implant of the type having upper and lower parts which engage adjacent vertebrae and a third part located between the upper and lower parts, the instrument comprising, an upper arm for holding the upper part at its free end and a lower arm for holding the lower part at its free end, a mounting structure for connecting the upper and lower arms together at their other ends remote from their free ends, such that the other ends are spaced apart vertically from each other and pivotally supported to allow their free ends to pivot towards and away from each other, and a spreader element engaging and movable along the upper and lower arms in one direction to spread them apart to thereby spread apart the upper and lower parts, and in the other direction to allow the upper and lower arms to come together and thereby allow the upper and lower parts to move towards each other.

56. The invention according to claim 55, the lower arm comprising a pair of parallel legs, the upper part comprising a single rod located centrally between the legs of the lower arm, said mounting structure comprising a bottom plate to which the parallel legs are connected and an upright mounting block, and the upper arm being pivotally connected to said mounting block at a pivot axis spaced above the bottom plate.

57. The invention according to claim 56, said spreader element including a toothed rack, a toothed gear wheel pivotally mounted on the mounting block and engaging the rack of the spreader element, whereby turning of the gear wheel moves the spreader element along the arms.

58. The invention according to claim 56, including a pusher mounted on the arms to move the third part along the arms for insertion between the upper and lower parts as the spreader element spreads the arms and hence also the upper and lower parts.

59. An insertion instrument in combination with a three piece intervertebral implant of the type having upper and lower parts which engage adjacent vertebrae and a third part located between the upper and lower parts, an upper arm having an upper part at a free end thereof,
a lower arm having a lower part at a free end thereof,
the lower arm comprising a pair of parallel legs which engage the lower part at their free ends, and define between them a receiving chamber, the legs on the sides facing the receiving chamber including a structure which engages the lateral edges of a third part for movement of the third part along said legs, a pusher element mounted on the legs for pushing the third part therealong, and a spreader element mounted on and slidable along the upper and lower arms to spread them apart.

60. The invention according to claim 59 the upper and lower arms having pins at their outer ends which engage bores in the upper and lower parts, respectively, to retain the upper and lower parts on the arms.

61. The invention according to claim 60, the structure which engages the lateral edges of the third part comprising grooves which extend longitudinally along said legs, and the third part is a pivot element having lateral edges which engage said grooves, and wherein the pushing element also engages the grooves and is operable to move the pivot element along the arms and into a space between spread apart upper and lower parts.

62. The invention according to claim 61, wherein the lower part has parallel grooves in the side walls thereof which are aligned with the grooves in the legs, whereby the pivot element can move directly from the grooves in the legs into the grooves in the lower part.

63. A method for inserting a three piece intervertebral implant into an intervertebral space, comprising the steps of:

assembling upper and lower parts of the intervertebral implant together and inserting them into an intervertebral space with an inserting instrument such that the upper surface of the upper part and the lower surface of the lower part engage adjacent vertebrae, after the upper and lower parts are located in the intervertebral spaces, spreading them apart, and with the upper and lower parts spread apart, moving a longitudinal guide along the inserting instrument to move a third part into the space between the upper and lower parts.

64. A method according to claim 63, wherein the step of moving the longitudinal guide includes placing the third part into grooves in the insertion instrument, and moving a pusher along those same grooves to move the third part out of the insertion instrument and into the intervertebral space between the spread apart upper and lower parts.

65. A method according to claim 64, wherein the step of causing the insertion instrument to spread apart the upper and lower parts includes moving a spreader along the insertion instrument to spread apart the upper and lower arms of the insertion instrument, the upper arm holding the upper part and the lower arm holding the lower part.

66. A method for inserting a three piece intervertebral implant into an intervertebral space, comprising the steps of:

assembling upper and lower parts of the intervertebral implant on an inserting instrument and inserting them into an intervertebral space, wherein the lower part has a recess, inserting the upper and lower parts into the intervertebral space, spreading the upper and lower parts apart by a distance slightly greater than the clearance between the lowermost surface of the upper part and the recess of the lower part, and moving the third part onto the recess of the lower part.

67. A method according to claim 66, wherein the insertion instrument has a lower arm comprising a pair of parallel legs with grooves on facing sides thereof, the lower part being held at the free ends of the parallel legs and the lower part having grooves in two parallel raised side walls adjacent an open side, which grooves are aligned with the grooves of the parallel legs, and wherein the step of moving the third part into the recess of the lower part comprises moving the third part along the grooves of the parallel legs and into the grooves of the lower part.

68. A method according to claim 67, wherein the insertion instrument also includes an upper arm which engages the upper part at a free end thereof and the step of spreading the upper and lower parts apart including moving a spreader along the insertion instrument towards the free ends thereof between the upper and lower arms to spread them apart.

69. A method according to claim 68, wherein the step of moving the upper part against the top of the third part includes moving the spreader in a direction away from the free ends.

70. An insertion device in combination with an intervertebral implant of the type having opposed vertebrae engaging upper and lower parts and an insert therebetween, comprising:
  an instrument for holding and inserting the upper and lower parts into an intervertebral space, and a spreader for separating the upper and lower parts while in the intervertebral space, and
  a pusher guided by the instrument to push the insert into the space between the separated upper and lower parts.

71. The invention according to claim 70, wherein one of the pusher and instrument has lateral edges and the other has grooves such that the lateral edges and the grooves cooperate for guiding the pusher along the instrument.

72. The invention according to claim 71, wherein the pusher has the lateral edges which engage grooves in the instrument.

73. The invention according to claim 70, wherein the instrument has upper and lower arms for engaging, respectively, the upper and lower parts and including a spread movable along the instrument to separate the upper and lower arms.

74. The invention according to claim 70, wherein the instrument has upper and lower arms which are spaced apart and operatively pivotally engaged to each other at a location spaced from the upper and lower part engaging ends of the instrument.

75. The invention according to claim 70, wherein the instrument has upper and lower arms for engaging the upper and lower parts, the lower arm having a pair of legs and wherein the pusher is mounted on the pair of legs for movement therealong.

76. The invention according to claim 75, including a spreader for spreading the upper and lower arms apart, and wherein the spreader is also mounted for movement along the pair of legs.

77. A method of inserting an intervertebral implant of the type comprising opposed vertebrae engaging upper and lower parts and an insert therebetween, comprising the steps of:
  holding the upper and lower parts with an instrument and inserting the upper and lower parts into an intervertebral space,
  spreading the upper and lower parts away from each other, and
  guiding a pusher on the instrument to push an insert into the space between the upper and lower parts.

78. The method according to claim 77, wherein the step of guiding the pusher on the instrument comprises engaging the pusher and the instrument together by lateral edges and groove connections, one of said lateral edge or groove on the instrument and the other on the pusher.

79. The method according to claim 78, wherein the lateral edges are on the pusher and the grooves are in the instrument.

80. The method according to claim 77, wherein the spreading step includes moving a spreader along the instrument to separate the upper and lower arms and hence the upper and lower parts.

81. The method according to claim 80, wherein the instrument includes upper and lower arms engaging, respectively, the upper and lower parts, and the separating step includes moving a spreader along the instrument to spread the upper and lower arms and hence the upper and lower parts.

* * * * *

UNITED STATES PATENT AND TRADEMARK OFFICE
CERTIFICATE OF CORRECTION

| | | |
|---|---|---|
| PATENT NO. | : 7,118,580 B1 | Page 1 of 1 |
| APPLICATION NO. | : 10/070823 | |
| DATED | : October 10, 2006 | |
| INVENTOR(S) | : Beyersdorff et al. | |

It is certified that error appears in the above-identified patent and that said Letters Patent is hereby corrected as shown below:

Claim 28, column 10, line 28, after "insertion" insert --instrument--;

Claim 30, column 10, line 46, after "both" insert --the--;

Claim 45, column 12, line 17, change "11" to --44--;

Claim 63, column 14, line 34, change "spaces" to --space--; and

Claim 73, column 15, line 36, change "spread" to --spreader--.

Signed and Sealed this

Ninth Day of January, 2007

JON W. DUDAS
*Director of the United States Patent and Trademark Office*